United States Patent
Miyamoto et al.

(10) Patent No.: US 10,571,427 B2
(45) Date of Patent: Feb. 25, 2020

(54) MOLECULAR DETECTION APPARATUS

(71) Applicant: KABUSHIKI KAISHA TOSHIBA, Minato-ku (JP)

(72) Inventors: Hirohisa Miyamoto, Kamakura (JP); Ko Yamada, Yokohama (JP); Reiko Yoshimura, Kawasaki (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 15/432,521

(22) Filed: Feb. 14, 2017

(65) Prior Publication Data

US 2018/0080897 A1 Mar. 22, 2018

(30) Foreign Application Priority Data

Sep. 20, 2016 (JP) .................. 2016-182745

(51) Int. Cl.
| | | |
|---|---|---|
| *G01N 27/414* | (2006.01) | |
| *G01N 1/34* | (2006.01) | |
| *G01N 27/27* | (2006.01) | |

(52) U.S. Cl.
CPC ........... *G01N 27/4148* (2013.01); *G01N 1/34* (2013.01); *G01N 27/27* (2013.01); *G01N 27/4145* (2013.01); *G01N 27/4146* (2013.01)

(58) Field of Classification Search
CPC ...... G01N 27/4148; G01N 27/27; G01N 1/34; G01N 27/128; G01N 27/4141;
(Continued)

(56) References Cited

U.S. PATENT DOCUMENTS

| | | |
|---|---|---|
| 5,541,851 A | 7/1996 | Sato et al. |
| 8,394,330 B1 | 3/2013 | Lewis et al. |
| (Continued) | | |

FOREIGN PATENT DOCUMENTS

| | | |
|---|---|---|
| JP | 7-198641 | 8/1995 |
| JP | 2002-508064 A | 3/2002 |
| (Continued) | | |

OTHER PUBLICATIONS

Extended European Search Report dated Apr. 13, 2017 in Patent Application No. 17155881.0.
(Continued)

*Primary Examiner* — Didarul A Mazumder
*Assistant Examiner* — Patricia D Reddington
(74) *Attorney, Agent, or Firm* — Oblon, McClelland, Maier & Neustadt, L.L.P.

(57) ABSTRACT

A molecular detection apparatus according to an embodiment includes: a collection unit collecting detection target gas containing molecules to be detected; a detector including a plurality of detection cells each having an organic probe disposed at a sensor unit, the organic probe capturing the molecules collected in the collection unit; and a discriminator discriminating the molecules by a signal pattern based on an intensity difference of detection signals generated by the molecules being captured by the organic probes in a plurality of the detection cells. In the molecular detection apparatus according to the embodiment, at least one of the detection cells has a plurality of different types of the organic probes disposed at the sensor unit.

14 Claims, 6 Drawing Sheets

(58) Field of Classification Search
CPC ............. G01N 33/037; G01N 27/4146; G01N 27/4145; Y10S 977/762; Y10S 977/957
USPC .......................................................... 257/414
See application file for complete search history.

(56) References Cited

U.S. PATENT DOCUMENTS

| | | | |
|---|---|---|---|
| 9,011,779 | B1 | 4/2015 | Anglin, Jr. et al. |
| 2002/0121440 | A1 | 9/2002 | Morris |
| 2008/0063566 | A1 | 3/2008 | Matsumoto et al. |
| 2008/0116490 | A1* | 5/2008 | Stewart ................. G01N 27/128 257/210 |
| 2012/0055236 | A1 | 3/2012 | Takulapalli |
| 2012/0058350 | A1* | 3/2012 | Long ...................... B82Y 10/00 428/446 |
| 2013/0273665 | A1* | 10/2013 | Swager ................... G01N 27/12 436/142 |
| 2014/0162390 | A1* | 6/2014 | Afzali-Ardakani ......................... G01N 33/5438 438/49 |
| 2015/0338390 | A1* | 11/2015 | Anglin, Jr. ........... G01N 33/497 73/23.3 |
| 2015/0364340 | A1 | 12/2015 | Ueda |
| 2016/0155948 | A1* | 6/2016 | Murase .................. B82Y 15/00 422/69 |
| 2017/0038333 | A1* | 2/2017 | Turner ............... G01N 27/4145 |

FOREIGN PATENT DOCUMENTS

| | | |
|---|---|---|
| JP | 2002-526769 | 8/2002 |
| JP | 2004-523731 | 8/2004 |
| JP | 2008-216083 | 9/2008 |
| JP | 2010-19688 | 1/2010 |
| JP | 2010-25719 | 2/2010 |
| JP | 2010-38569 | 2/2010 |
| JP | 2010-38840 | 2/2010 |
| JP | 2010-139269 | 6/2010 |
| JP | 2010-530063 | 9/2010 |
| JP | 2011-80798 | 4/2011 |
| JP | 2012-247189 | 12/2012 |
| JP | 2014-521081 | 8/2014 |
| JP | WO 2015/012186 | 1/2015 |
| JP | WO 2016/031080 A1 | 3/2016 |
| WO | WO 99/00663 | 1/1999 |
| WO | WO 2006/025481 A1 | 3/2006 |
| WO | WO 2013/008062 A1 | 1/2013 |
| WO | WO 2017/025996 A1 | 2/2017 |

OTHER PUBLICATIONS

Beibei Zhan, et al., "Graphene Field-Effect Transistor and Its Application for Electronic Sensing" Small, XP055200050, Jul. 7, 2014, pp. 1-24 and Cover Page.

Gugang Chen et al. "Sub-ppt gas detection with pristine graphene," Applied Physics Letters 101, 053119, http://dx.doi.org/10.1063/1.4742327, 2012, pp. 5.

* cited by examiner

MOLECULAR DETECTION APPARATUS

CROSS-REFERENCE TO RELATED APPLICATION

This application is based upon and claims the benefit of priority from Japanese Patent Application No. 2016-182745 filed on Sep. 20, 2016; the entire contents of which are incorporated herein by reference.

FIELD

Embodiments described herein generally relate to a molecular detection apparatus.

BACKGROUND

In recent years, global environmental problems due to an air pollution have become obvious, and in the context to tightening of regulations on emission gas from plants and vehicles, a gas detection apparatus has been required to be highly sensitive. In terms of an environmental standard related to the air pollution, for example, 40 ppb (parts per billion) or less has served as a standard for $NO_X$ (nitrogen oxide), and thus, detecting an extremely small amount of gas component in the order of ppb has been required. Separately from the environmental problems, in the defense field, development of accurate and rapid analytical methods with respect to NBC (Nuclear Biological Chemical) substances has stood as an issue. In terms of chemical agents in particular, rapid sensing of toxic gas that has an extremely strong effect on human body has been required as seen in the sarin nerve-gas attack on the Tokyo subway system. In order to prevent secondary damage, it is necessary to detect a gas component having an extremely low concentration in real time. Although various methods have been known as a method of detecting a gas component having a relatively high concentration, the detection methods have been limited for detecting the gas component having a concentration of ppb (parts per billion) to ppt (parts per trillion), which corresponds to an extremely low concentration.

For example, at a disaster site or a site at which an act of terrorism occurs or the like, it has been desired to sense the risk in advance by detecting an extremely small amount of the gas component. The gas component having an extremely low concentration is often detected by use of a large equipment in research facilities. In this case, a large sized installation type equipment, which is expensive and has large weight and volume, such as a gas chromatography or a mass spectrometer, is required. The case when direct measurement is desired on the go relies on a simple measurement method that detects the gas component by use of a biological reaction mechanism, but has many problems of a storage life, temperature management, a limit of determination whether the gas component is present or not, and the like. Under such circumstances, it has been required to provide an apparatus that is capable of detecting the gas component having an extremely low concentration in real time, in other words, an apparatus that has a smaller weight and volume and a better portability and enables selective and higher sensitive detection of the gas component having an extremely low concentration in the order of ppt to ppb.

As a detection element for the gas component having a low concentration, for example, an element has been known that has a conductive layer in which a surface of a carbon nanostructure is surface modified with an organic substance or the like that selectively reacts with or adsorbs a specific substance and measures a potential difference or the like that changes depending on the gas component that has adhered to the surface of the carbon nanostructure. When a component or the like similar to detection target gas component is mixed, as an impurity, in gas obtained from the air, such a detection element has a risk of being incapable of accurately detecting the detection target gas component. Further, types of the organic substance that reacts with or adsorbs the detection target gas component (gas molecules) themselves are also limited and only the modification of the surface of the carbon nanostructure or the like with the organic substance is not sufficient, resulting in a difficulty in further increasing detection accuracy of the gas component.

DETAILED DESCRIPTION

According to an embodiment, a molecular detection apparatus is provided. The molecular detection apparatus includes: a collection unit collecting detection target gas containing molecules to be detected; a detector including a plurality of detection cells each having a sensor unit and an organic probe disposed at the sensor unit, the organic probe capturing the molecules collected in the collection unit; and a discriminator discriminating the molecules by a signal pattern based on an intensity difference of detection signals generated by the molecules being captured by the organic probes in a plurality of the detection cells. In the molecular detection apparatus according to the embodiment, at least one of the detection cells has a plurality of different types of the organic probes disposed at the sensor unit.

Hereinafter, a molecular detection apparatus according to embodiments will be explained with reference to the drawings. In each embodiment, substantially the same constituent elements are denoted by the same reference signs and an explanation thereof will be omitted in some cases. The drawings are schematic, and a relation of the thickness and the planar dimension of each unit, a thickness ratio of each unit, and so on may differ from actual ones.

Figure 1:
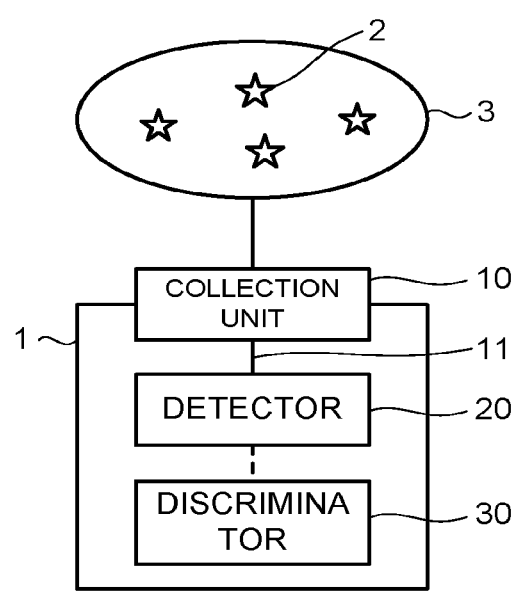
FIG. 1 is a block diagram illustrating a molecular detection apparatus according to an embodiment.

FIG. 1 is a block diagram illustrating a molecular detection apparatus according to the embodiment. A molecular detection apparatus 1 illustrated in FIG. 1 is, for example, an apparatus that detects, from detection target gas 3 containing molecules to be detected (substances to be detected) 2 generated from a gas generation source, the molecules to be detected 2, and includes a collection unit 10, a detector 20, and a discriminator 30. The detection target gas 3 containing the molecules to be detected (gas molecules to be detected) 2 is, first collected by the collection unit 10 in the molecular detection apparatus 1. The collection unit 10 has a collection port for the detection target gas 3 and is connected to the detector 20 via a gas flow channel 11. The collection unit 10 may include a filter for removing impurities such as fine particles contained in the detection target gas 3.

Figure 2:
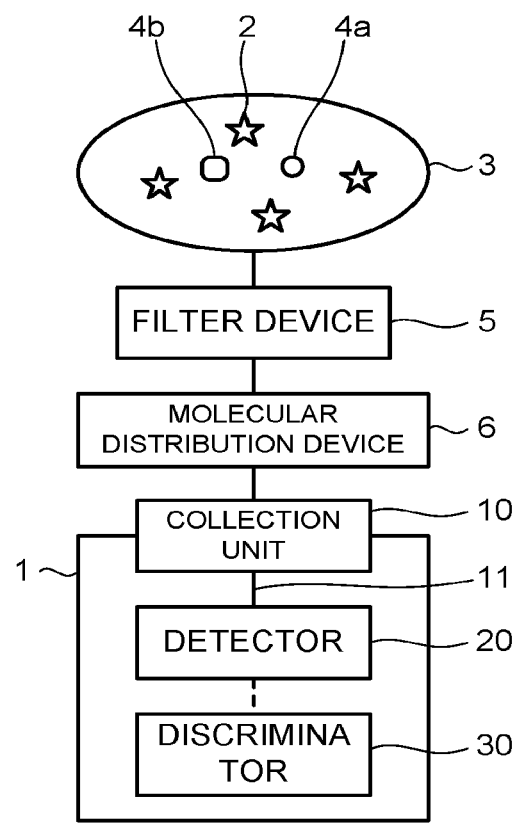
FIG. 2 is a block diagram illustrating a modified example to the molecular detection apparatus shown in FIG. 1.

The detection target gas 3 sometimes contains, as an impurity, substances having a molecular weight, a molecular structure or the like similar to that of the molecule to be detected 2. Further, as illustrated in FIG. 2, the molecules to be detected 2 drifting in the air often exist in a state where the molecules to be detected 2 are mixed with various foreign substances 4 (4a and 4b) such as an odor component and a fine particle. From those perspectives, as illustrated in FIG. 2, the detection target gas 3 may be sent to the molecular detection apparatus 1 after being preprocessed by a filter device 5, a molecular distribution device 6, and the like beforehand.

For the filter device 5 out of the devices of preprocess, a generally-used moderate-to-high performance filter or the like is used. The filter device 5 removes particulate substances such as fine particles contained in the detection target gas 3. The detection target gas 3, from which the particulate substances are removed in the filter device 5, is then sent to the molecular distribution device 6. As the molecular distribution device 6, there can be cited an apparatus that ionizes the detection target gas 3 to form an ionized substance group, applies voltage to the ionized substance group to allow the ionized substance group to fly at a speed proportional to the mass thereof, and separates an ionized substance of the molecules to be detected 2 from the ionized substance group using a flight speed based on the difference in mass among ionized substances and a time of flight based on the flight speed. As the molecular distribution device 6 as above, a device including an ionization unit, a voltage application unit, and a time-of-flight separation unit is used.

Figure 3:
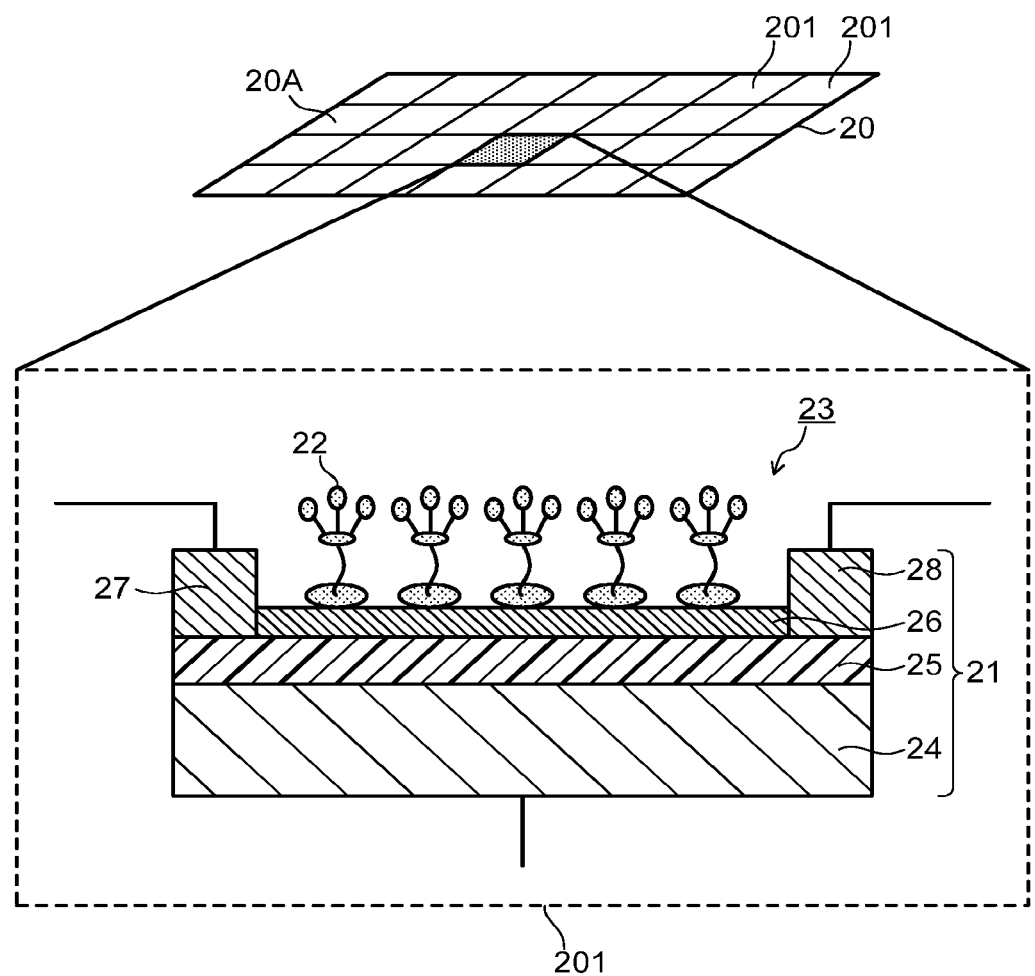
FIG. 3 is a view illustrating a configuration of a detector according to the embodiment.

The detection target gas 3 containing the molecules to be detected 2 is collected by the collection unit 10 directly, or is collected by the collection unit 10 after being preprocessed by the devices such as the filter device 5 and the molecular distribution device 6. The molecules to be detected 2 collected by the collection unit 10 are then sent to the detector 20 thorough the gas flow channel 11. The detector 20, as illustrated in FIG. 3, includes a detection surface 20A sectioned into a plurality of detection cells 201. The detection surface 20A of the detector 20 is disposed towards an output port (not illustrated), for the molecules to be detected 2, of the gas flow channel 11. The plural detection cells 201 each include a detection element 23 having a sensor unit 21 and organic probes 22 provided at the sensor unit 21. FIG. 3 illustrates the detection element 23 using a graphene field effect transistor (GFET) for the sensor unit 21.

The GFET serving as the sensor unit 21 includes a semiconductor substrate 24 that functions as a gate electrode, an insulating film 25 disposed as a gate insulating layer on the semiconductor substrate 24, a graphene layer 26 disposed as a channel on the insulating film 25, a source electrode 27 provided at one end of the graphene layer 26, and a drain electrode 28 provided at the other end of the graphene layer 26. The organic probes 22 are disposed on the graphene layer 26. As will be described later, on the graphene layer 26 of the GFET of at least one of the plural detection cells 201, a plurality of types of organic probes comprised of different types of organic compounds are provided. The molecules to be detected 2 that are led into the detector 20 are captured by the organic probes 22 on the graphene layer 26. Electrons are moved from the molecules to be detected 2 captured by the organic probes 22 to the GFET 21, thereby performing electric detection. In this way, the intended molecules to be detected 2 are detected.

When the molecules to be detected 2 are captured by the organic probes 22 disposed on the graphene layer 26, an output from the GFET 21 changes. The case of a single layer of graphene means that there is zero gap, and thus, the source electrode 27 and the drain electrode 28 are continuously electrified normally. When the number of graphene layers increases to two or three layers, a band gap is generated, but such a band gap in an actual system is relatively smaller than that considered from a strict theoretical value. When the gate insulating layer 25 has a dielectric constant approximately similar to that of a silicon dioxide film, the source electrode 27 and the drain electrode 28 are often continuously electrified. Thus, the graphene layer 26 may be formed of a stack composed of about five graphene layers or less as well as the single layer structure of graphene.

The molecules to be detected 2 flying in the vicinity of the organic probe 22 are attracted to the organic probe 22 by hydrogen bonding force or the like, or comes into contact with the organic probe 22 in some cases. When the contact with the molecules to be detected 2 occurs, an interchange of electrons occurs with the organic probe 22 and the organic probe 22 transmits an electrical change to the graphene layer 26 being in contact therewith. The electrical change transmitted from the organic probe 22 to the graphene layer 26 disturbs the flow of electricity between the source electrode 27 and the drain electrode 28, and thus the GFET 21 functions as a sensor.

With the GFET 21 using the graphene layer 26 as a channel, even an extremely slight electrical change appears significantly as an output. As a result, it is possible to constitute the highly sensitive detection element 23. The sensor using the GFET 21 also has a tendency that electric current flows between the source electrode 27 and the drain electrode 28 without application of voltage to the gate electrode 24 because the graphene has a property as a zero-gap semiconductor. Thus, the GFET 21 functions as a sensor as it is. However, normally, in the GFET 21 electric current is applied between the source electrode 27 and the drain electrode 28 in a state of applying voltage to the gate electrode 24, and an electrical change of the gate electrode 24 is observed when the organic probe 22 captures the molecules to be detected 2.

In the detection of the molecules to be detected 2 performed by the above-described detection element 23, as the movement of electrons from the molecules to be detected 2 that is captured by the organic probe 22 to the GFET 21 is higher, the function as the sensor is further increased. The sensor using the GFET 21 is regarded as the most sensitive FET sensor, and can improve sensitivity about three times as compared to a sensor using a carbon nanotube. Thus, using the detection element 23 in which the GFET 21 and the organic probe 22 are combined enables higher sensitive detection of the molecules to be detected 2. FIG. 3 illustrates the detection surface 20A on which the plural detection cells 201 are arranged in a grid pattern (an array pattern), but is not necessarily limited thereto. The plural detection cells 201 may be arranged linearly.

Figure 8:
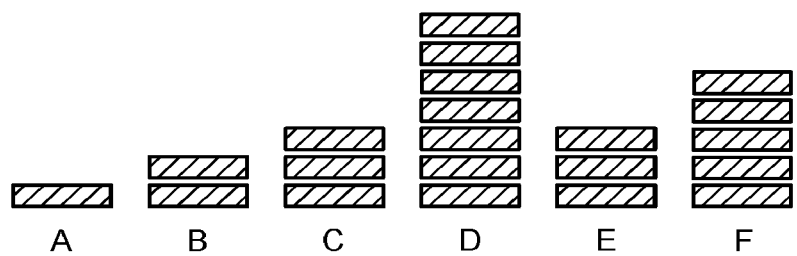
FIG. 8 is a view illustrating a first example of detection results of molecules to be detected illustrated in FIG. 7.
Figure 9:
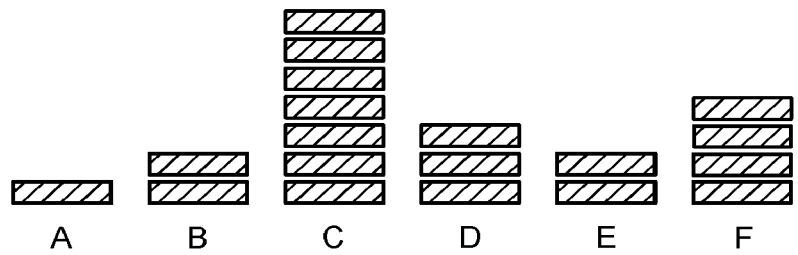
FIG. 9 is a view illustrating a second example of the detection results of the molecules to be detected illustrated in FIG. 7.

The organic probes 22 disposed on the graphene layers 26 in the plural detection cells 201 are different in working strength (bond strength) with the molecules to be detected 2 respectively. As above, the organic probes 22 in the plural detection cells 201 have different working strengths (bond strengths) with the molecules to be detected 2 respectively. Thereby, even when the same molecules to be detected 2 are detected by the plural detection cells 201, detection signals by the respective detection cells 201 differ in intensity. Accordingly, signals detected in the respective detection cells 201 are sent to the discriminator 30 to be signal-processed and the detection signals are converted into signal intensities, thereby obtaining such signal patterns based on intensity differences of the detection signals as illustrated in FIG. 8 or FIG. 9 that will be described later. The discriminator 30 stores therein signal patterns according to substances (molecules) to be detected, and compares the stored signal patterns and the detected signal patterns, to thereby discriminate the molecules to be detected 20 detected in the detector 20. Such a signal process is called a pattern recognition method here. The pattern recognition method enables detection and discrimination of the molecules to be detected 2 by the signal patterns peculiar to the substance to be detected like a dactyloscopy, for example.

When detecting and discriminating the molecules to be detected 2 by the pattern recognition method, it is necessary to make the working strengths (bond strengths) of the organic probes 22 in the plural detection cells 201 with the molecules to be detected 2 differ. As the organic probes 22 different in the working strength with the molecules to be detected 2, a plurality of different types of organic compounds are considered. That is, it is possible to consider providing a plurality of different types of organic compounds different in the working strength with the molecules to be detected 2 at the graphene layers 26 of the plural detection cells 201 as the organic probes 22 respectively. In this case, a signal intensity when one type of the molecules to be detected 2 is detected in the single detection cell 201 becomes a value according to the working strength of the organic compound as the organic probe 22 with the molecules to be detected 2 to be a fixed signal intensity. By changing the density of the organic probes 22 on the graphene layer 26, the signal intensity can also be changed, but the installation density of the organic probes 22 still has difficulty in sufficiently increasing the intensity difference of the detection signal. The signal intensity based on the type of organic compound as the organic probe 22 is based on the working strength with the molecules to be detected 2 according to the type of organic compound, and thus it is impossible to change the signal intensity intentionally.

Figure 4:
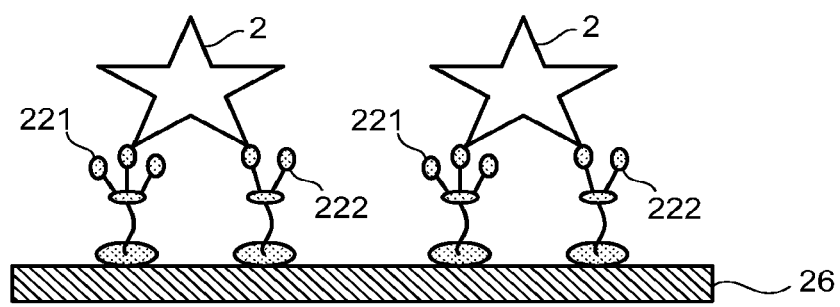
FIG. 4 is a view illustrating a first installation example of organic probes according to the embodiment.
Figure 5:
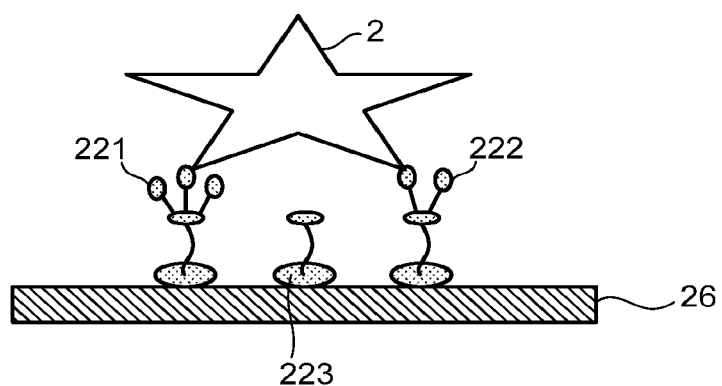
FIG. 5 is a view illustrating a second installation example of the organic probes according to the embodiment.

Thus, in the molecular detection apparatus 1 according to the embodiment, as illustrated in FIG. 4 and FIG. 5, a plurality of types of organic probes 221 and 222 comprised of different types of organic compounds are disposed on the graphene layer 26 forming the single detection cell 201. FIG. 4 illustrates an example where a plurality of types of the organic probes 221 and 222 each having reactivity with the molecules to be detected 2 and different in reaction strength (working strength) with the molecules to be detected 2 are disposed on the graphene layer 26 forming the single detection cell 201. FIG. 5 illustrates an example where on the graphene layer 26 forming the single detection cell 201, an organic probe 223 having no reactivity with the molecules to be detected 2 is disposed, in addition to the organic probes 221 and 222 different in reaction strength (working strength) with the molecules to be detected 2. A plurality of types of the organic probes 22 disposed on the graphene layer 26 of the single detection cell 201 may employ either a combination of a plurality of types of the organic probes 221 and 222 different in the reaction strength with the molecules to be detected 2 or a combination of the organic probes 221 and 222 having reactivity with the molecules to be detected 2 and the organic probe 223 having no reactivity with the molecules to be detected 2.

In FIG. 4, first organic probes 221 and second organic probes 222 are provided on the graphene layer 26 forming the single detection cell 201. The first organic probes 221 and the second organic probes 222 are comprised of different types of organic compounds respectively. Although the first and second organic probes 221 and 222 each have an interaction (reactivity) with the molecules to be detected 2, their bond strengths with the molecules to be detected 2 are different according to the types of organic compounds forming the organic probes 221 and 222. A mixing ratio of such organic probes 221 and 222 is varied in the plural detection cells 201, thereby making it possible to intentionally change the intensity of the detection signal when capturing the molecules to be detected 2 according to the mixing ratio of the organic probes 221 and 222. That is, it is possible to arbitrarily fabricate the detection cells 201 different in the bond strength with the molecules to be detected 2.

Intentionally changing the intensity of the detection signal according to the mixing ratio of the organic probes 221 and 222 makes it possible to increase accuracy of such signal patterns based on the intensity differences of the detection signals in a manner to correspond to the molecules to be detected 2 as illustrated in FIG. 8 or FIG. 9 to be described later. Further, it is also possible to make reaction points of the organic probes 221 and 222 with the molecules to be detected 2 differ according to the types of organic compounds. Using the plural organic probes 221 and 222 having different reaction points with the molecules to be detected 2 makes it possible to increase selectivity of the molecules to be detected 2 and at the same time, improve a property of capturing the molecules to be detected 2 by the detection cell 201 and the signal intensity when capturing the molecules to be detected 2. This also makes it possible to increase accuracy of the signal patterns corresponding to the molecules to be detected 2. Accordingly, it is possible to improve discrimination accuracy of the molecules to be detected 2 when discriminating the molecules to be detected 2 by the signal patterns based on the intensity differences of the detection signals in the plural detection cells 201.

In FIG. 5, a first organic probe 221, a second organic probe 222, and a third organic probe 223 are provided on the graphene layer 26 forming the single detection cell 201. The first and second organic probes 221 and 222 are similar to the organic probes 221 and 222 illustrated in FIG. 4. The third organic probe 223 does not exhibit an interaction with the molecules to be detected 2, and functions as a spacer between the first and second organic probes 221 and 222. Using such a third organic probe 223 makes it possible to change a width of reaction points with the molecules to be detected 2 between the first and second organic probes 221 and 222, or the like. This also makes it possible to increase the capturing property and the selectivity of the molecules to be detected 2. Accordingly, it becomes possible to improve discrimination accuracy of the molecules to be detected 2. It is also possible to mix the organic probe 223 that does not exhibit an interaction with the molecules to be detected 2 and the organic probe 221 (or 222) that exhibits an interaction with the molecules to be detected 2 to increase the capturing property and the selectivity of the molecules to be detected 2.

As a method of providing a plurality of types of the organic probes 22 (221, 222, or 221, 222, and 223) on the graphene layer 26 while changing the mixing ratio of them, for example, the following solution method can be applied. That is, the organic compound forming the organic probe 22 has a property of dissolving in a solvent, and thus solutions in which a plurality of types of organic compounds are dissolved are made and such solutions are applied, thereby enabling installation of a plurality of types of the organic probes 22 at the graphene layer 26. On this case, with use of solutions obtained by changing the mixing ratio of a plurality of types of the organic compounds, a plurality of types of the organic probes 22 can be provided on the graphene layer 26 at a desired mixing ratio.

When a plurality of types of the organic probes 22 are provided on the graphene layer 26 by applying the solution method, a plurality of types of the organic probes 22 each preferably include a portion having such a structure as a pyrene ring in order to easily obtain an interaction with graphene. A molecule having such a structure as a pyrene ring has an interaction with a hexagonal π-electron system formed by carbon of the graphene, and forms an interaction state of what is called π-π stacking. Low-concentration probe molecules are dissolved in a solvent and the resultant is applied to the graphene, and thereby the π-π stacking is formed between the pyrene ring and the graphene and the probe molecules are aligned on the graphene to be fixed. By using such a self-alignment action, a plurality of types of the organic probes 22 can be installed on the graphene layer 26. The organic probe 223 that does not exhibit an interaction with the molecules to be detected 2 also preferably has a pyrene ring or the like. This enables the organic probe 223 to be installed on the graphene layer 26.

Figure 6:
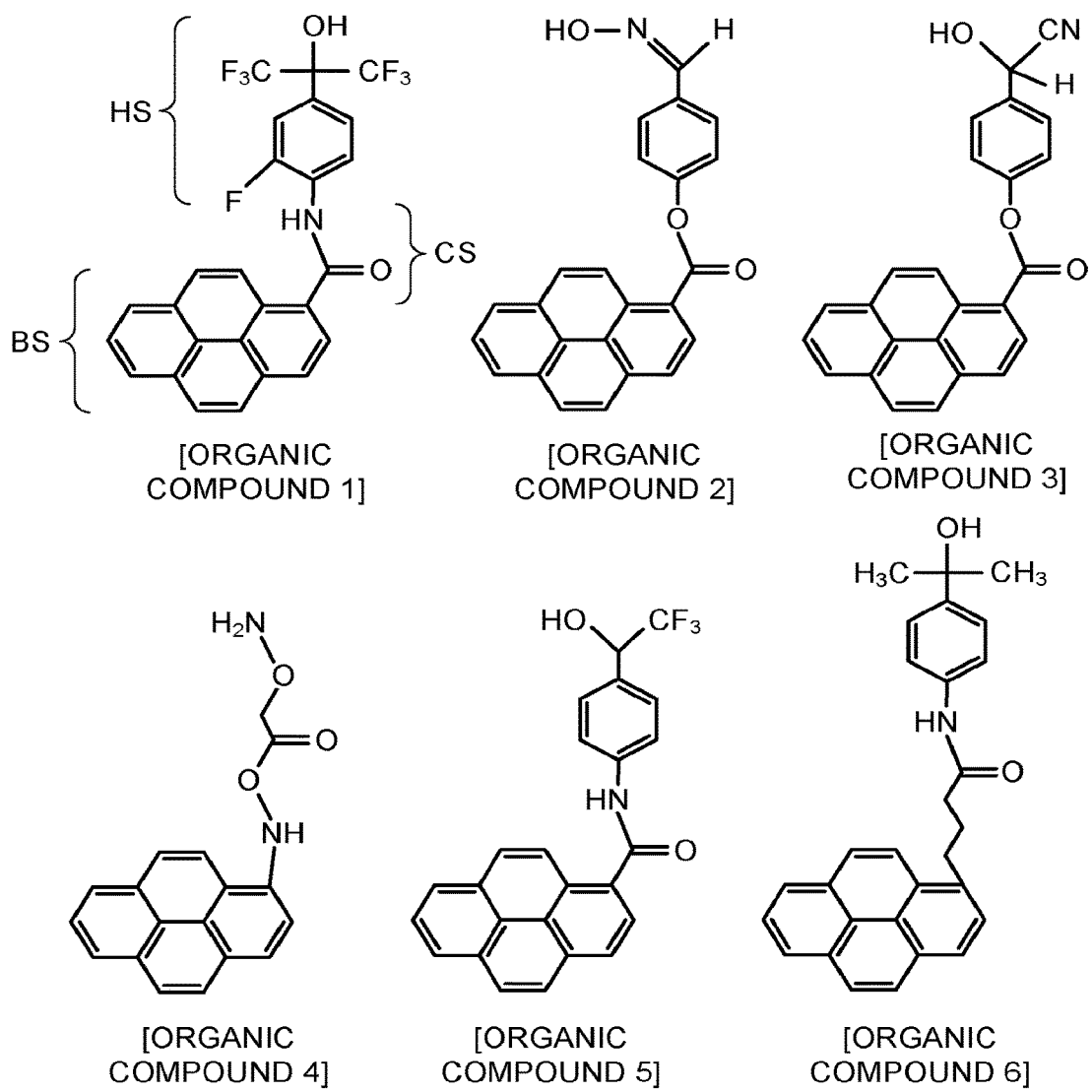
FIG. 6 is a view illustrating examples of organic compounds used for the organic probes according to the embodiment.

Next, there is explained a concrete composition example of the organic probe 22. For the organic probe 22, for example, an organic compound having, as a reactive group with respect to the molecules to be detected 2, a hydroxy group (—OH), an amino group (—NH$_2$), or the like is used. FIG. 6 illustrates examples of the organic probe 22. Among organic compounds forming the organic probes 22, organic compounds 1 to 3, and 5 and 6 each have a hydroxy group as the reactive group with respect to the molecules to be detected 2. The organic compound 4 has an amino group as the reactive group. However, only the reactive group hardly reacts with the gas component. For the purpose of enhancing a hydrogen bonding property or the like, it is preferred to use an organic compound with a functional group (neighboring group) having an excellent effect of inducing the molecules to be detected 2 introduced into a portion adjacent to the reactive group.

As the neighboring group to the hydroxy group (—OH) being the reactive group, there can be cited a fluorinated alkyl group such as a trifluoromethyl group (—CF$_3$) or a hexafluoroethyl group (—C$_2$F$_5$), a functional group containing nitrogen such as a cyano group (—CN), a nitro group (—NO$_2$), or a —CHN group, and an alkyl group such as a methyl group (—CH$_3$) or an ethyl group (—C$_2$H$_5$). The organic compounds 1 and 5 have the trifluoromethyl group (—CF$_3$) as the neighboring group to the reactive group (—OH). The organic compound 2 has a —CHN—OH group as the functional group containing the reactive group. The organic compound 3 has the cyano group (—CN) as the neighboring group to the reactive group (—OH). The organic compound 6 has the methyl group (—CH$_3$) as the neighboring group to the reactive group (—OH). As the neighboring group to the amino group (—NH$_2$) being the reactive group, an ether linkage group (—O—) can be cited. The organic compound 4 has an —O—NH$_2$ group as the functional group containing the reactive group. As the functional group containing the reactive group, a phosphate group (H$_2$PO$_4$—), a phosphonate group (H$_2$PO$_3$—), or the like may be used. The neighboring group preferably bonds to the same carbon as the reactive group. One type or two or more types of these may be used.

The organic compounds 1 to 6 illustrated in FIG. 6 are examples of the organic compounds forming the organic probes 22, and the organic probes 22 are not limited to the organic compounds 1 to 6. The organic probe 22 is preferably formed of an organic compound that has a head portion HS having an organic group containing the reactive group such as the hydroxy group or the amino group and the above-described neighboring group, a base portion BS serving as an installation portion for the graphene layer 26 or the like, and a connecting portion CS connecting the head portion HS and the base portion BS. The head portion HS is preferred to be an aromatic hydrocarbon group having the reactive group and the neighboring group, and further preferred to be a phenyl group having an alkyl group in which the reactive group and the neighboring group are bonded to the same carbon (carbon number: about 1 to 5).

The base portion BS is preferred to be a substituted or unsubstituted polycyclic aromatic hydrocarbon group having a polycyclic structure such as a pyrene ring, an anthracene ring, a naphthacene ring, or a phenanthrene ring, and further preferred to be a substituted or unsubstituted pyrene group. The connecting portion CS is a single bond or an organic group. The organic group may be a substituted or unsubstituted alkylene group such as a methylene group or an ethylene group, but is preferred to be an ether bond (—O—), an ester bond (—C(=O) O—), a carbonyl bond (—CO—), an amide bond (—NH—CO—), an imide bond (—CO—NH—CO—) or the like, or a substituted or unsubstituted alkylene group containing these groups. Further, it is more preferred to be the amide bond or a group containing the amide bond.

In the above-described organic compound forming the organic probe 22, the bond strength of the organic probe 22 with the molecules to be detected 2 can be adjusted according to the type of reactive group, the type of neighboring group to the reactive group, the number of them, or the like. For example, the neighboring group (CH$_3$ group) of the organic compound 6 is different in type from the neighboring group (CF$_3$ group) of the organic compound 1. The trifluoromethyl group has an effect of enhancing activity of the reactive group (OH group) with fluorine having a high electronegativity, but such an effect of the methyl group is low. Accordingly, the bond strength with the molecules to be detected 2 can be made different. The organic compound 5 is different from the organic compound 1 in the number of neighboring groups (CF$_3$ group), and thus is different in the bond strength with the molecules to be detected 2 therefrom. The organic compounds 2 to 4 are different from the organic compound 1 in the type of functional group containing the reactive group, and thus are different in the bond strength with the molecules to be detected 2 therefrom.

A mixture of a plurality of types of the organic probes 22 comprised of the above-described organic compounds that are different in the type of reactive group, the type of neighboring group, the number of neighboring groups, or the like is provided on the graphene layer 26 forming the single detection cell 201. Then, by changing the mixing ratio of a plurality of types of the organic probes 22 in the plural detection cells 201, the working strength (bond strength) with the molecules to be detected 2 in each of the detection cells 201 and the detection signal intensity based on the work strength (bond strength) can be adjusted. In other words, a plurality of types of the organic probes 22 with changed mixing ratios are provided in each of the plural detection cells 201, and thereby it is possible to arbitrarily obtain the plural detection cells 201 that are different in the bond strength with the molecules to be detected 2 and are different in the detection signal intensity based on the bond strength, according to the mixing ratio of a plurality of types of the organic probes 22.

A plurality of types of the organic probes 22 with changed mixing ratios do not need to be applied to all the detection cells 201 forming the detector 20, and may be applied to some of the detection cells 201. For example, the detector 20 may include the plural detection cells 201 having a plurality of types of the organic probes 22 with changed mixing ratios and the detection cell 201 having only one of a plurality of types of the organic probes 22, or the detection cell 201 having the organic probe 22 comprised of an organic compound different from them. The constitutions of the organic probes 22 provided in the plural detection cells 201 forming the detector 20 are arbitrary, and at least one of the detection cells 201 only needs to have a plurality of types of the organic probes 22. The detector 20 is preferably formed in which at least two of the detection cells 201 each have a plurality of types of the organic probes 22 and the mixing ratio of a plurality of types of the organic probes 22 is different between the two.

Figure 7:
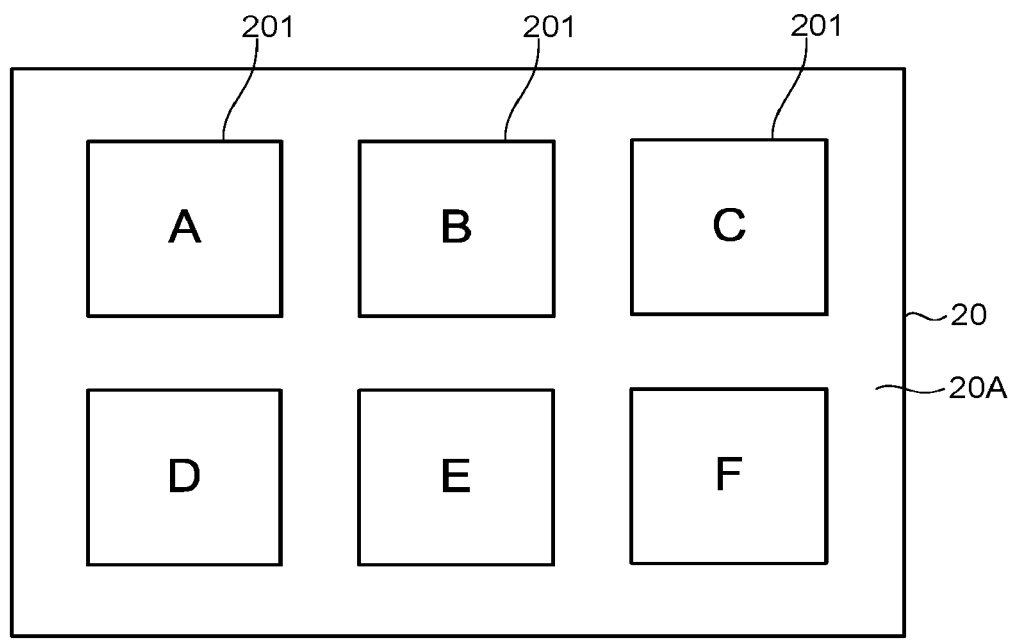
FIG. 7 is a view illustrating one example of detection cells according to the embodiment.

FIG. 7 illustrates a grid-shaped sensor in which the detection surface 20A of the detector 20 is sectioned into six detection cells 201, namely a detection cell A, a detection cell B, a detection cell C, a detection cell D, a detection cell E, and a detection cell F. At least in some of the detection cells A to F, a plurality of types of the organic probes 22 different in the bond strength with the molecules to be detected 2 are provided, and they are different in the mixing ratio. For example, in the six detection cells A to F, the first organic probe 221 and the second organic probe 222 are installed while changing the mixing ratio of them to six stages. On this case, a detection cell having only the first organic probe 221 or the second organic probe 222 may be provided. The six detection cells A to F are different in the working strength (bond strength) with the molecules to be detected 2 according to the mixing ratio of the first organic probe 221 and the second organic probe 222, and thus are different in the intensity of the detection signal of the molecules to be detected 2. In this manner, according to the mixing ratio of the two organic probes 22, the bond strength with the molecules to be detected 2 and the signal intensity based on the bond strength are adjusted.

Signals detected in the detection cells A to F are sent to the discriminator 30 to be signal-processed. The discriminator 30 converts the detection signals from the detection cells A to F into intensities and obtains signal patterns based on intensity differences of these detection signals. FIG. 8 and FIG. 9 each illustrate one example of the signal patterns obtained from the detection cells A to F. Such signal patterns are analyzed. The discriminator 30 stores therein signal patterns according to a substance to be detected and compares these signal patterns and the signal patterns detected in the detection cells A to F, to thereby discriminate the molecules to be detected 2 detected in the detector 20. FIG. 8 and FIG. 9 illustrate signal patterns of two types of the molecules to be detected 2. In this manner, the signal patterns according to the type of the molecules to be detected 2 can be obtained. On this occasion, the intensity of the detection signal of the molecules to be detected 2 can be adjusted according to the mixing ratio of a plurality of types of the organic probes 22, thus making it possible to increase the contrast of the signal intensity and improve recognition accuracy of the signal pattern based on the contrast. Accordingly, selective and higher sensitive detection of a gas component having an extremely low concentration in the order of ppt to ppb (the molecules to be detected 2) is enabled.

As described above, by applying the pattern recognition method using the plural detection cells 201 in which a plurality of types of the organic probes 22 are provided while changing the mixing ratio of these, selective and higher sensitive detection and discrimination of the molecules to be detected 2 are enabled even when impurities are mixed in the detection target gas 3 that is led to the detector 20. For example, in the case when the molecule to be detected 2 is dimethyl methylphosphonate (DMMP, molecule weight: 124), which is a typical material for a toxic organophosphorus compound, there exist agricultural chemicals containing phosphoric acid such as dichlorvos having a similar chemical structure and organophosphorous pesticides, which are used often, such as malathion, chlorpyrifos, and diazinon. In order to prevent an erroneous detection of these substances, discrimination by such signal patterns as illustrated in FIG. 8 and FIG. 9 is effective. In other words, since the signal patterns detected in the detection cells A to F are different due to the above-described respective substances, application of the pattern recognition method enables selective and higher sensitive detection of the detection target substance even when an impurity that has a similar molecular weight and a similar constituent element is mixed. Further, a plurality of types of the organic probes 22 are used to increase reaction points with the molecules to be detected 2, thereby making it to possible to increase selectivity when the organic probe 22 captures the molecules to be detected 2. Consequently, it is possible to more selectively detect the detection target substance.

According to the molecular detection apparatus 1 of the embodiment, application of the pattern recognition method enables selective and higher sensitive detection of gas molecules having an extremely low concentration in the order of ppt to ppb. Further, by using the plural detection cells 201 in which a plurality of types of the organic probes 2 are provided while changing the mixing ratio of these, the contrast of the signal intensity and the recognition accuracy of the signal pattern based on the contrast can be improved. Accordingly, it is possible to further increase detection sensitivity and detection reliability of gas molecules having an extremely low concentration. Further, increasing the detection sensitivity and the detection accuracy of the detector 20 enables miniaturization of the molecular detection apparatus 1. Accordingly, it becomes possible to provide the molecular detection apparatus 1 with portability and detection accuracy both achieved. Such a molecular detection apparatus 1 effectively fulfills its function at various field sites such as a disaster site or a site of an act of terrorism.

Next, specific examples and evaluation results thereof will be described.

Example 1

A detection element in which a GFET and an organic probe are combined is prepared as follows. First, graphene is formed on a surface of a copper foil by CVD (Chemical Vapor Deposition) with flowing of a gas containing a hydrocarbon-based substance such as methane under the condition of about 1000° C. Next, a polymethyl methacrylate film is applied at 4000 rpm by a spin coating method, and the opposite surface of the copper foil is etched with an ammonium persulfate solution of 0.1 M, and thereby a graphene film floating in the solution is recovered. By doing this, the graphene is transferred onto the polymethyl methacrylate film side.

A surface of the graphene is sufficiently cleaned, and then this is transferred again onto a silicon substrate having a $SiO_2$ film formed on a surface thereof. After the redundant polymethyl methacrylate film is removed, a resist is applied onto the graphene transferred onto the silicon substrate to undergo patterning, and an electrode pattern is formed by oxygen plasma. Electrode materials are vapor-deposited so as to obtain a source-drain interval of 10 nm, thereby forming an FET structure having a source electrode and a drain electrode. In this way, the graphene is disposed on an oxidized film formed on the surface of the silicon substrate, and a sensor structure having a back gate GFET is formed in which the graphene is sandwiched between the source electrode and the drain electrode and the silicon substrate side is set as a gate electrode.

Next, an organic probe is provided on the surface of the graphene. The organic probe is installed in a manner that an organic compound is dissolved in a methanol solution with a concentration of 10 nM and a graphene sensor surface is immersed in the resultant solution for several minutes. In Example 1, as illustrated in FIG. 7, six detection cells A to F are provided on a detection surface of a detector, and a mixture of two types of organic compounds is installed in the respective detection cells as the organic probe. As the two types of organic compounds, the organic compound 1 and the organic compound 4 illustrated in FIG. 6 are used. Only the organic compound 1 is provided in the detection cell A, and only the organic compound 4 is provided in the detection cell F. In the detection cell B, a mixture obtained by mixing the organic compound 1 and the organic compound 4 at a molar ratio of 8:2 is provided. In the same manner, in the detection cells C, D, and E, a mixture obtained by mixing the organic compound 1 and the organic compound 4 at a molar ratio of 6:4, a mixture obtained by the organic compound 1 and the organic compound 4 at a molar ratio of 4:6, and a mixture obtained by mixing the organic compound 1 and the organic compound 4 at a molar ratio of 2:8 are provided respectively. The detection cells A to F are different in bond strength with the gas molecules to be detected according to the mixing ratio of the organic compound 1 and the organic compound 4. A chamber covers the GFET having the organic probes, to thereby form the detector.

As the gas molecule to be detected, dimethyl methylphosphonate (DMMP, molecular weight 124), which is an alternative gas to a toxic organophosphorus compound, is used. The DMMP being an alternative substance to be detected is liquid at normal temperature and has a flash point of 69° C. and a boiling point of 181° C. A vapor pressure is 79 Pa (20° C.). The DMMP has a stable property as a liquid at normal temperature. In order to evaporate such a liquid, it is general to promote evaporation by increasing temperature. However, as a simpler method, there is employed a method of performing what is called bubbling in which an inert gas is supplied into a liquid for increasing the surface area of the liquid, a method of promoting evaporation by blowing gas onto the surface of a liquid, or the like. The concentration of gas obtained in this manner is about ppm to ppb, and the obtained gas is mixed with the inert gas, thereby enabling a further reduction in concentration of the gas.

In Example 1, by a blowing method with use of a nitrogen ($N_2$) gas, a DMMP-containing gas with a DMMP concentration of 80 ppb is prepared. A pump exhausts air from the chamber installed to cover the GFET having the organic probes of the detector, and then the DMMP-containing gas is introduced into the chamber. Before and after the introduction of the DMMP-containing gas, a drain current when a back gate voltage is swept between −100 V and +100 V under a fixed drain voltage and each time response of the drain current under a fixed drain voltage and a fixed back gate voltage are measured. The relative signal intensity patterns illustrated in FIG. 8 are obtained as the recognition results by the six detection cells. Detection of the DMMP is confirmed from the signal intensity patterns illustrated in FIG. 8. As illustrated in FIG. 8, it is possible to increase the contrast of the signal intensities from the respective detection cells. Accordingly, an improvement in detection accuracy of the molecules to be detected is enabled.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The inventions described in the accompanying claims and their equivalents are intended to cover such forms or modifications as would fall within the scope and spirit of the inventions.

What is claimed is:

1. A molecular detection apparatus, comprising:
    a detector including a plurality of detection cells each having one sensor unit and an organic probe disposed at the sensor unit, the organic probe capturing molecules to be detected,
    wherein
    at least two of the detection cells has a plurality of different types of the organic probes disposed at its respective one sensor unit, and the plurality of organic probes comprises a first organic probe which reacts to a first part of one of the molecules to be detected and a second organic probe which reacts to a second part, which is different from the first part, of the one of the molecules to be detected, and
    a mixing ratio of the plurality of types of the organic probes is different between at least two of the detection cells.

2. The molecular detection apparatus of claim 1, wherein the sensor unit comprises a field effect transistor including
    a graphene layer and a source electrode and a drain electrode both connected to the graphene layer, and
    the organic probe is disposed on the graphene layer.

3. The molecular detection apparatus of claim 1, wherein a plurality of types of the organic probes have different reactivity with the molecules to be detected.

4. The molecular detection apparatus of claim 1, further comprising:
    a collection unit collecting detection target gas containing the molecules to be detected.

5. The molecular detection apparatus of claim 1, further comprising:
    a discriminator discriminating the molecules by a signal pattern based on an intensity difference of detection signals generated by the molecules being captured by the organic probes in a plurality of the detection cells.

6. The molecular detection apparatus, comprising:
a detector including a plurality of detection cells each having one sensor unit and an organic probe disposed at the sensor unit, the organic probe capturing molecules to be detected, wherein
at least one of the detection cells has a plurality of different types of the organic probes disposed at its respective one sensor unit, and the plurality of organic probes comprises a first organic probe which reacts to a first part of one of the molecules to be detected and a second organic probe which reacts to a second part, which is different from the first part, of the one of the molecules to be detected, and
at least one of the plurality of types of the organic probes has reactivity with the molecules to be detected, and at least another one of the plurality of types of the organic probes does not have reactivity with the molecules to be detected.

7. The molecular detection apparatus of claim 6, wherein
the sensor unit comprises a field effect transistor including a graphene layer and a source electrode and a drain electrode both connected to the graphene layer, and
the organic probe is disposed on the graphene layer.

8. The molecular detection apparatus of claim 6, further comprising:
a collection unit collecting detection target gas containing the molecules to be detected.

9. The molecular detection apparatus of claim 6, further comprising:
a discriminator discriminating the molecules by a signal pattern based on an intensity difference of detection signals generated by the molecules being captured by the organic probes in a plurality of the detection cells.

10. The molecular detection apparatus, comprising:
a detector including a plurality of detection cells each having one sensor unit and an organic probe disposed at the sensor unit, the organic probe capturing molecules to be detected, wherein
at least one of the detection cells has a plurality of different types of the organic probes disposed at its respective one sensor unit, and the plurality of organic probes comprises a first organic probe which reacts to a first part of one of the molecules to be detected and a second organic probe which reacts to a second part, which is different from the first part, of the one of the molecules to be detected, and
each of the organic probes is comprised of an organic compound having: a head portion having an organic group containing a reactive group and a neighboring group that is disposed at a portion adjacent to the reactive group and has an effect of inducing the molecules to be detected; a base portion having a polycyclic aromatic hydrocarbon group; and a connecting portion having a single bond or an organic group connecting the head portion and the base portion, and
the plurality of types of the organic probes are comprised of organic compounds having different types of the reactive groups, or organic compounds different in at least one of a type and a number of neighboring groups.

11. The molecular detection apparatus of claim 10, wherein
the reactive group is at least one selected from a hydroxy group and an amino group, and
the neighboring group is at least one selected from a fluorinated alkyl group, an alkyl group, a cyano group, a nitro group, and an ether linkage group.

12. The molecular detection apparatus of claim 10, wherein
the sensor unit comprises a field effect transistor including a graphene layer and a source electrode and a drain electrode both connected to the graphene layer, and
the organic probe is disposed on the graphene layer.

13. The molecular detection apparatus of claim 10, further comprising:
a collection unit collecting detection target gas containing the molecules to be detected.

14. The molecular detection apparatus of claim 10, further comprising:
a discriminator discriminating the molecules by a signal pattern based on an intensity difference of detection signals generated by the molecules being captured by the organic probes in a plurality of the detection cells.

* * * * *